United States Patent
McConnell

(10) Patent No.: US 10,072,191 B2
(45) Date of Patent: Sep. 11, 2018

(54) COMPOSITION, SYSTEM AND METHOD FOR PREVENTING FORMATION OF FROZEN WATER OR FOR CAUSING THE SAME TO MELT

(71) Applicant: ESSECO UK LIMITED, Wakefield (GB)

(72) Inventor: Alistair McConnell, Wakefield (GB)

(73) Assignee: ESSECO UK LIMITED, Wakefield (GB)

( * ) Notice: Subject to any disclaimer, the term of this patent is extended or adjusted under 35 U.S.C. 154(b) by 435 days.

(21) Appl. No.: 14/409,572

(22) PCT Filed: Jun. 24, 2013

(86) PCT No.: PCT/GB2013/051646
§ 371 (c)(1),
(2) Date: Dec. 19, 2014

(87) PCT Pub. No.: WO2013/190331
PCT Pub. Date: Dec. 27, 2013

(65) Prior Publication Data
US 2015/0184046 A1   Jul. 2, 2015

(30) Foreign Application Priority Data
Jun. 22, 2012   (GB) .................... 1211059.9

(51) Int. Cl.
C09K 3/00 (2006.01)
C09K 3/18 (2006.01)
G01N 33/00 (2006.01)
G01N 33/18 (2006.01)

(52) U.S. Cl.
CPC ............... *C09K 3/18* (2013.01); *C09K 3/185* (2013.01); *G01N 33/00* (2013.01); *G01N 33/18* (2013.01)

(58) Field of Classification Search
CPC ..................................................... C09K 3/18
USPC ........................................................ 436/56
See application file for complete search history.

(56) References Cited

U.S. PATENT DOCUMENTS

| 3,756,956 A | * | 9/1973 | Panusch ................... C09K 3/18 252/389.2 |
| 3,928,654 A | * | 12/1975 | Bonnanzio ............. C09K 3/185 106/13 |
| 4,032,090 A | * | 6/1977 | Thornton-Trump ...... B64F 5/20 106/13 |
| 4,254,166 A | * | 3/1981 | Glanville ................. C09K 3/18 106/13 |
| 5,039,439 A | | 8/1991 | Hansman et al. |
| 2003/0071241 A1 | | 4/2003 | Kyoon et al. |

FOREIGN PATENT DOCUMENTS

| CA | 2269398 A1 | 10/1996 |
| EP | 0870813 A1 | 10/1998 |
| FR | 2792324 A1 | 10/2000 |
| WO | 0146334 A1 | 6/2001 |

OTHER PUBLICATIONS

International Preliminary Report on Patentability dated Dec. 23, 2014 in related International Patent Application No. PCT/GB2013/051646.
Search Report in related GB Application No. GB1211059.9, dated Oct. 23, 2012.
International Search Report and Written Opinion in related PCT Application No. PCT/GB2013/051646, dated Jan. 3, 2014.

* cited by examiner

*Primary Examiner* — Christine T Mui
*Assistant Examiner* — Emily R. Berkeley
(74) *Attorney, Agent, or Firm* — Troutman Sanders LLP; Ryan A. Schneider

(57) ABSTRACT

A de/anti-icer composition comprises one or more de/anti-icer moieties and a marker material, the marker material being selected such that, after application of the de/anti-icer composition to a traveled surface, the amount of the marker material at or on the traveled surface at a given time correlates to the amount of said one or more de/anti-icer moieties on the said surface at such time. The presence of the marker material enables the user readily to determine the concentration of the de/anti-icer moiety or the freezing point of liquid on the traveled surface. Methods of using such compositions for concentration and/or freezing point determination of de/anti-icer materials applied to traveled surfaces are described, together with systems and kits of parts utilizing such compositions.

14 Claims, No Drawings

COMPOSITION, SYSTEM AND METHOD FOR PREVENTING FORMATION OF FROZEN WATER OR FOR CAUSING THE SAME TO MELT

CROSS-REFERENCE TO RELATED APPLICATIONS

This application is a US National Stage of International Application No. PCT/GB2013/051646, filed 24 Jun. 2013, which claims the benefit of GB Application No. 1211059.9, filed 22 Jun. 2012, both herein fully incorporated by reference.

BACKGROUND

Technical Field

Embodiments of the present invention relate to compositions for application to traveled surfaces for preventing the formation of frozen water, such as ice or snow, on the traveled surface and/or for causing existing frozen water, such as ice or snow, on the traveled surface to melt.

Embodiments of the present invention can also relate to apparatus and systems for determining the amount of a de-icer or anti-icer composition present on a traveled surface and/or for determining the freezing point of liquid on the traveled surface.

Embodiments of the present invention relate to methods for determining the amount of a de-icer or anti-icer composition present on a traveled surface and/or for determining the freezing point of liquid on the traveled surface.

Background of Related Art

Chemical de-icing and anti-icing treatments are routinely used in freezing weather conditions, notably in the winter and in cold climates, to prevent the formation or build up of snow and/or ice on surfaces traversed by pedestrians or vehicles, such as on paths, pavements (sidewalks), stairways, roads, airport taxiways, aprons and runways and the like. Such compositions act by melting existing snow and ice, or by preventing the formation of ice or the settling or build-up of snow, on the surface to which the treatment is applied.

The desirability of maintaining traveled surfaces free from ice, snow or other frozen water (typically derived from freezing precipitation) is well known and understood. Numerous treatments for traveled surfaces are known in the art which are, to a greater or lesser extent, effective in melting ice and snow, or in preventing the formation of ice and snow on the traveled surface.

Known de/anti-icer compositions include freezing point depressant materials as the de/anti-icer moieties or moieties. Numerous freezing point depressant materials are known in the art.

Many prior art de/anti-icer compositions for use on traveled surfaces have contained ethylene glycol. Although ethylene glycol-containing compositions demonstrate high performance with regard to de-icing and anti-icing ability, they also suffer from several significant disadvantages. Any de/anti-icer composition applied to a traveled surface is likely to be washed off the surface by water from melting snow and ice and/or by rainwater. The de/anti-icer composition is thus brought into contact with the wider environment. Ethylene glycol is toxic to humans and numerous cases of poisoning have been reported in the UK and worldwide. Furthermore, ethylene glycol-based de/anti-icers have a high Chemical Oxygen Demand (COD) and thus exhibit deleterious effects when exposed to the wider environment following their application. As a result, the use of ethylene glycol has been prohibited in aircraft de-icing fluids in Europe and at some airports in North America.

Alternative de-icer compositions include those with urea as the active ingredient. However, urea-based de-icer compositions have a highly adverse environmental impact due to their very high COD and by acting as a rich source of nitrogen. Urea-based de-icer compositions are therefore highly damaging to any watercourses which receive run-off from the surface to which the de-icer is applied. In addition, the suitability of urea-based compositions as effective de-icers is compromised by a comparatively high minimum effective temperature of −12° C. (10° F.) which is insufficiently low in colder climates where ground temperatures lower than this minimum effective temperature are often encountered.

In an effort to overcome the disadvantages of ethylene glycol-containing and urea-containing products, de/anti-icing compositions based on 50% w/w aqueous solution of potassium acetate are now used at airports in cold winter climates around the world. Potassium acetate solution can be combined with suitable corrosion inhibitors and meets the high standards of non-corrosiveness to aircraft materials required for airside use, and the COD and Biological Oxygen Demand (BOD) load in water run-off generated by potassium acetate based products is much lower than ethylene glycol or urea-based compositions.

De-icing or anti-icing compositions based on 50% w/w aqueous solution of potassium formate are also used at the airside parts of airports and function in the same way as 50% w/w potassium acetate based fluids but have even lower COD and BOD values.

Embodiments of the present invention can be used in conjunction with such known de-icer or anti-icer compositions (but not exclusively in conjunction with such known compositions) to ensure that only the minimum necessary amount (to achieve the required de-icing or anti-icing effect) of the composition is applied to the traveled surface, thereby to reduce wastage and to avoid or limit possible environmental damage.

A particular problem which arises in relation to the application of de/anti-icer compositions to traveled surfaces is in determining whether an application of the de/anti-icer composition to the traveled surface is, or continues to be, effective. For example, it may be that the de/anti-icer composition is applied to the traveled surface at a given rate appropriate to weather conditions prevailing at the time application, following which the weather conditions become colder, to the extent that the amount of the applied de/anti-icer composition is (at least potentially) insufficient to prevent freezing of water on the traveled surface. Again, it may be that the de/anti-icer composition is applied to the traveled surface at a given rate initially appropriate to prevailing weather conditions, following which there is snowfall and the amount of the applied de/anti-icer composition is (at least potentially) insufficient to melt the snow and prevent its accumulation on the traveled surface. The de/anti-icer composition may be displaced from the traveled surface by the passage of vehicles. Moreover, the de/anti-icer composition applied to the traveled surface may become diluted over time either because of rainfall or by virtue of the melting of the frozen water (ice, snow etc) on the traveled surface by the de/anti-icer composition. Dilution of the de/anti-icer composition reduces the freezing point depressing effect. Also, on dilution, since the de/anti-icer composition becomes dissolved in water on the traveled surface it tends to be carried away from the surface as water run-off.

The concentration (amount) of de/anti-icer composition available on the traveled surface for melting (further) ice or snow is thus reduced and the de/anti icing effect correspondingly reduces, or may indeed be eliminated.

As a result, it is important to understand and/or to be aware when the freezing point of liquid on a traveled surface is approaching ambient temperature so that action can be taken to prevent liquid on the traveled surface from freezing. Said freezing point may approach the ambient temperature because of a lessening freezing point depression on dilution of the de/anti-icer moiety and/or because ambient temperatures become colder.

For the above reasons it is important to be able to determine the amount of de/anti-icer composition remaining on a traveled surface at a given time, to be sure that the remaining amount of de/anti-icer composition is sufficient to effect the required degree of de/anti-icing of the traveled surface, taking into account, for example, the likely usage of the traveled surface and the prevailing or expected weather conditions.

However, determining the remaining amount of de/anti-icer composition on the traveled surface is not easy and more especially is not easily achieved in a way which is simple to carry out and which provides reliable results in a short timescale. For example, simple visual inspection of the surface is usually not adequate or reliable as a means of determining whether an appropriate amount of de/anti-icer composition remains on the traveled surface. This can be due to prevailing weather, hours of darkness, or the simple fact that particular de/anti icer material being used is not discernible to the naked eye.

Furthermore, de/anti-icer compositions based on potassium acetate and/or potassium formate are virtually indistinguishable (on visual inspection) from water when on a traveled surface.

Available laboratory methods for analysing freezing point of, for example, potassium acetate or formate concentration of a solution (from which freezing point can be calculated) are not suitable for adaptation to the field environment (i.e. to a traveled surface such as an airport runway), for reasons such as the practical impossibility of collecting suitable samples from the traveled surface, the cost and non-availability of analytical equipment and the non-availability of suitably trained staff. Real-time systems for measuring the potassium acetate or formate concentration in material on the runway surface, based on conductivity probes embedded in the runway surface, have been installed at some airports. The performance and utility of these systems is generally excellent, however such systems are prohibitively expensive for most airports, especially for airports located in areas, such as the U.K, where very cold winters are not an annual occurrence.

Many locations, and most notably airports, therefore, have no sure way of knowing when re-application of a de/anti-icing composition is actually required in winter conditions, and must instead rely mainly or wholly on experience and 'educated guesses'. This approach is not satisfactory. This approach leaves the airport or other body responsible for the safe operation of a traveled surface at high risk of the traveled surfaces (runways and taxiways) freezing over suddenly. This can lead to accidents such as aircraft overruns or to temporary airport closure. Conversely de/anti-icing compositions will inevitably be applied in circumstances where the application was in fact unnecessary, resulting significant unnecessary expenditure per application, as well as an unnecessary environmental impact even when the de/anti-icer composition is based on materials having a relatively low environmental impact such as acetate or formate.

Embodiments of the present invention, therefore, seek to resolve, or at least mitigate or moderate, the above problems in determining whether, when and/or how much de/anti icer product should be applied or re-applied.

BRIEF SUMMARY

Embodiments of the present invention can comprise a de/anti-icer composition that can comprise one or more de/anti-icer moieties, and a marker material. In some embodiments, the marker material can be selected such that, after application of the de/anti-icer composition to a traveled surface, an amount of the one or more de/anti-icer moieties proximate the traveled surface at a given time can be determined from an amount of the marker material proximate the traveled surface at the given time.

Embodiments of the present invention can also comprise a reader apparatus that can comprise a processor and a memory. In some embodiments, the memory can comprise logical instructions that, when executed by the processor, can cause the reader to obtain a sample from a surface to which a de/anti-icing composition can comprise one or more de/anti-icing moieties and a marker material, determine the quantity of the marker material in the sample, calculate the amount of the one or more de/anti-icing moieties in the sample based on the quantity of the marker material in the sample, and provide a user-interpretable output of the amount of the one or more de/anti-icing moieties in the sample.

Embodiments of the present invention can also comprise a system for enabling a user to determine a quantity of one or more de/anti-icer moieties on a traveled surface. The system can comprise: (i) a de/anti-icer composition for application to the traveled surface that can comprise one or more de/anti-icer moieties and a marker material, and (ii) a reader apparatus. In some embodiments, the reader apparatus can be configured to obtain a sample from a surface to which a de/anti-icing composition comprising one or more de/anti-icing moieties and a marker material, determine the quantity of the marker material in the sample, calculate the amount of the one or more de/anti-icing moieties in the sample based on the quantity of the marker material in the sample, and provide a user-interpretable output of the amount of the one or more de/anti-icing moieties in the sample.

In some embodiments, the marker material can be selected from the group consisting of glucose, alcohols, completely or partially water soluble salts of aluminum, ammonia or ammonium salts, ascorbic acid, completely or partially water soluble salts of calcium, carbonic acid salts, iodine, iodide salts, chlorine, chloride salts, bromine, bromide salts, fluorine, fluoride salts, completely or partially water soluble salts of cobalt, completely or partially water soluble salts of copper, formaldehyde, paraformaldehyde, reducing sugars other than glucose, starch, glutardialdehyde, ketones, aldehydes, completely or partially water soluble salts of iron, completely or partially water soluble salts of manganese, completely or partially water soluble salts of molybdenum, completely or partially water soluble salts of nickel, nitrate salts of one or more of potassium, sodium, lithium, magnesium, calcium, aluminum, iron and zinc, nitrite salts of one or more of potassium, sodium, lithium, magnesium, calcium, aluminum, iron and zinc, salts of peracetic acid, hydrogen peroxide, organic peroxides, phosphate salts of one or more of potassium, sodium, lithium, magnesium, calcium, aluminum, iron and zinc, quaternary ammonium compounds, sulfate salts of one or more of potassium, sodium, lithium, magnesium, calcium, aluminum, iron and zinc, sulfite salts of one or more of potassium, sodium, lithium, magnesium, calcium, aluminum, iron and zinc, completely or partially water soluble salts of zinc, proteins, and peptides or amino acids.

In some embodiments, the marker material can be water soluble. In other embodiments, the marker material can be selected from the group consisting of glucose, completely or partially water soluble salts of iron, completely or partially water soluble salts of zinc, carbonic acid salts, formaldehyde, starch, and phosphate salts of one or more of potassium, sodium, lithium, magnesium and calcium. In some embodiments, the marker material can be present in an amount of from about 0.001% w/w to about 0.2% w/w.

In some embodiments, the one or more de/anti-icer moieties can be selected from the group consisting of ethylene glycol, propylene glycol, urea, alkali metal formate salts, alkali metal acetate salts and alkali metal acetate/formate salt mixtures. In other embodiments, the one or more de/anti-icer moieties can comprise one or more alkali metal formate salts. In some embodiments, the one or more de/anti-icer moieties can comprise one or more alkali metal acetate salts. In other embodiments, the one or more de/anti-icer moieties can comprise alkali metal acetate/formate salt mixtures.

In some embodiments, the alkali metal can be potassium or sodium. In some embodiments, the one or more de/anti-icer moieties can comprise at least about 25% w/w of at least one acetate salt selected from the group consisting of potassium, sodium, lithium, magnesium, calcium, ammonium acetate and mixtures thereof, and from about 14% to about 50% w/w of at least one non-acetate salt that can comprise one or more cations selected from the group consisting of: potassium, sodium, lithium, magnesium, calcium, ammonium and mixtures thereof and one or more anions selected from the group consisting of formate, propionate, butyrate, isobutyrate, oxalate, malonate, succinate, glutarate, adipate, citrate, gluconate, benzoate, carbonate, bicarbonate, fluoride, chloride, bromide and mixtures thereof, wherein the total concentration of the at least one acetate salt and the at least one non-acetate salt in the de/anti-icer composition can be at least about 57% w/w.

Embodiments of the present invention can further comprise a solvent and/or not more than about 5% w/w in total of one or more auxiliary or incidental additives.

Embodiments of the present invention can also comprise a method of determining a quantity of one or more de/anti-icer moieties in a liquid on a traveled surface. In some embodiments, the method can comprise sampling the liquid on the traveled surface, and determining the quantity of the one or more de/anti-icer moieties in the sample, wherein the determining can comprise: determining a quantity of a marker material applied to the traveled surface contemporaneously with the one or more de/anti-icer moieties, and correlating the quantity of the marker material with the quantity of the one or more de/anti-icer moieties.

Other aspects and features of embodiments of the present disclosure will become apparent to those of ordinary skill in the art upon reviewing the following detailed description.

DETAILED DESCRIPTION

Embodiments of the invention seek to address the above problems by providing a de/anti-icer composition by use of which a user can readily determine, assess or judge, at a given time after application of the composition to a traveled surface, the amount of the one or more de/anti-icer moieties of the de/anti-icer composition remaining on the traveled surface. This can be achieved by including in the de/anti-icer composition a marker material the presence, absence, concentration or amount of which can be readily determined. From the determined remaining presence, absence, concentration or amount of the marker material, the remaining presence, absence, concentration or amount of the de/anti-icer material can be readily determined. Consequently, the freezing point of liquid on the traveled surface can also be determined.

The solution presented by certain embodiments of the present invention can include the provision of a de/anti-icer composition which can include a marker material. The de/anti-icer composition can include one or more de/anti-icer moieties (that is, the component or components of the composition included because of their de/anti-icing properties) and the marker material can be selected or configured such that its concentration at a given time after application of the composition to a traveled surface can correlate with or correspond to the concentration of the one or more de/anti-icer moieties. One distinct advantage of embodiments of the present invention is the ability to determine a quantitative value of the amount of de/anti-icer on a given surface.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity. For example, while the compositions disclosed herein are described for use with aircraft and related surfaces, they are equally applicable to automotive and domestic uses.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

As used herein, the terms "de/anti-icer", "de/anti-icer compositions" and "de/anti icing compositions" and linguistic or grammatical variants thereof refer to chemical compositions suitable for application to a surface to melt water present on the surface in frozen form (i.e. ice or snow), or to prevent the formation of ice or settling or accumulation of snow or other frozen or freezing precipitation on the surface in freezing conditions. Any given composition can be suitable for use only as a de-icer, only as an anti-icer, or as both a de-icer and an anti-icer depending, for example, on the nature of the surface to which the de/anti-icer composition is applied and the presence or absence of other formulation agents (such as corrosion inhibitors or viscosity modifiers, for example) which can render the composition suitable, or unsuitable, for application to a given surface.

Generally, the terms "de-icer", "de-icer composition" and "de-icing composition" and linguistic or grammatical variants thereof are used to refer to a chemical composition suitable for application to a surface to remove existing ice or snow or other frozen or freezing precipitation.

Generally the terms "anti-icer", "anti-icer composition" and "anti-icing composition" and linguistic or grammatical variants thereof are used to refer to a chemical composition suitable for application to a surface to prevent the formation of ice or settling of snow or other frozen or freezing precipitation.

In the context of the present application, frozen water is typically water from rain or other precipitation which has fallen on a surface and frozen due to prevailing atmospheric and/or ground surface temperatures. Such water can have fallen directly onto the traveled surface or can have flowed onto the surface from adjacent areas. Thus the frozen water can include rain which has frozen after arrival at the traveled surface. The frozen water can be present as a result of a weather episode such as snow, hail, freezing rain and the like.

As used herein, the term "traveled surface" and linguistic or grammatical variants thereof refers to a ground surface traversed by a pedestrian or by any type of land vehicle or by an aircraft when on the ground, and in particular to such surfaces where the presence or formation of frozen water such as ice or snow would limit, restrict, prevent, make hazardous or otherwise represent an increased danger to, the safe traversal of the surface by a pedestrian, land vehicle or aircraft.

The term "traveled surface" can also apply to any surface where, in freezing conditions (or in anticipation of freezing conditions), de-icer and/or anti-icer compositions are conventionally applied and more especially to such surfaces which are constructed for the specific purpose of traversal by pedestrians, land vehicles or aircraft when on the ground.

Examples of traveled surfaces include, without limitation, footpaths, footways and tracks, pavements (sidewalks), walkways, boardwalks, stairways, roads and highways, bridges, footbridges, car parks (parking lots), railways (railroads), railway stations (train stations) and platforms, tramways and tram stops, bus stops, airport taxiways, airport aprons and airport runways.

In further embodiments of the present invention, the term "traveled surface" refers in particular to any ground surface traversed by a vehicle at the "airside" part of an airport, including one or more of ground surfaces traversed by aircraft during take-off, landing and/or taxiing operations. "Travelled surface" refers especially to such surfaces at commercial airports. Thus "traveled surface" can refer in aspects and embodiments of the invention to any ground surface traversed by passenger- and/or freight-carrying commercial aircraft and notably to any such ground surface traversed by passenger- and/or freight-carrying commercial aircraft operating scheduled or charter services.

Other traveled surfaces traversed by aircraft within the ambit of the present invention can include runways and taxiing surfaces and apron areas at military airbases and at private airfields, aerodromes and flying clubs. Herein, aircraft can refer to either or both of fixed wing aircraft and rotary wing aircraft.

As used herein, in relation to a marker material or in relation to one or more de/anti-icer moieties, the term "quantity" refers to one or more of the presence, absence, concentration or amount of said marker material or of said de/anti-icer moiety/moieties. More especially, the term "quantity" refers to the one or more of the presence, absence, concentration or amount of said marker material or said one or more de/anti-icer moieties in a liquid on, or in a liquid sampled from, a traveled surface As used herein, a "marker material" is a material (notably a chemical compound) incorporated into a de/anti-icer composition containing one or more de/anti-icer moieties and where, following application of the de/anti-icer composition to a traveled surface, the quantity of the marker material in liquid of the traveled surface remains representative of the quantity of the one or more de/anti-icer moieties in that liquid. The quantity of the material remains representative in the sense that the quantity of the marker material in the liquid of the traveled surface can be used to determine (within practically acceptable tolerances) the quantity of the one or more de/anti-icer moieties in that liquid. Thus in embodiments, an amount of the one or more de/anti-icer moieties in liquid of the traveled surface at a given time can be determined from an amount of the marker in that liquid at the given time. "Liquid of the traveled surface" may be liquid on, proximate, or sampled from, the traveled surface.

In other words, the marker material is such that the quantity of the marker material at or on the traveled surface at a given time after application of a de-icer composition including the marker material correlates or corresponds to the amount of said one or more de/anti-icer moieties on the said surface at such time.

The "liquid sampled from a traveled surface" or "liquid on a traveled surface" is an aqueous solution resulting from the application of de/anti-icer composition to a traveled surface and comprising primarily of the de/anti-icer composition (including the one or more de/anti-icer moieties and the marker material) and water from the traveled surface, such water being present as a result of precipitation and/or melting (by the de-icer composition) of frozen water at the traveled surface.

According to a first aspect of the present invention there is provided a de/anti-icer composition comprising one or more de/anti-icer moieties and a marker material. The marker material can be selected such that, after application of the de/anti-icer composition to a traveled surface, the amount of the marker material at or on the traveled surface at a given time is representative of the amount of said one or more de/anti-icer moieties on the said surface at such time.

In some embodiments, the de/anti-icer composition is a liquid.

The composition can be such that a user-determination of the presence, absence, concentration or amount of said marker material informs the user of the respective presence, absence, concentration or amount of said one or more de/anti-icer moieties on the traveled surface.

In some embodiments, said user-determination of the presence, absence, concentration or amount of said marker material may be such as to inform the user directly of the freezing point of liquid on the traveled surface.

According to a second aspect of the present invention there is provided a reader apparatus operative to provide a user-interpretable output by which a user can determine a quantity of a de/anti-icing substance or moiety on a traveled surface to which traveled surface a composition comprising the one or more de/anti-icing moieties and a marker material has previously been applied. The reader apparatus can be configured to cooperate with said marker material to determine the quantity thereof and to provide said user-interpretable output based on the determination of the quantity of the marker material. In some embodiments, said user-interpretable output may inform the user directly of the freezing point of liquid on the traveled surface.

A third aspect of the present invention can also comprise a reader apparatus comprising a processor and memory comprising logical instructions that, when executed by the processor, can cause the reader to provide a user-interpretable output indicative of a quantity of a de/anti-icing substance or moiety on a traveled surface to which a composition comprising one or more de/anti-icing moieties and a marker material have previously been applied, can cooperate with the marker material to determine the quantity thereof, and can provide the user-interpretable output based on a determination of a quantity of the marker material.

According to a fourth aspect of the present invention there is provided a system for enabling a user to determine a quantity of one or more de/anti-icer moieties on a traveled surface. The system can comprise: (i) a de/anti-icer composition for application to the traveled surface comprising one or more de/anti-icer moieties and a marker material; and (ii) a reader apparatus configured to cooperate with the marker material to provide a user-interpretable output based on a determination of the quantity of the marker material on the traveled surface wherein the user interpretable output can be indicative the quantity of said one or more de/anti-icer moieties on said traveled surface at said given time.

In some embodiments, said user-interpretable output can inform the user directly of the freezing point of liquid on the traveled surface.

According to a fifth aspect of the present invention there is provided a method of determining the quantity of one or more de/anti-icer moieties in a liquid on a traveled surface. The method can comprise sampling the liquid on the traveled surface and determining the quantity of the one or more de/anti-icer moieties in the sample, wherein the determination can comprise determining the quantity of a marker material applied to the traveled surface contemporaneously with the of one or more de/anti-icer moieties and correlating the quantity of the marker material with the respective quantity of the one or more de/anti-icer moieties. In some embodiments, the step of correlating the quantity of the marker material can be a correlation with the freezing point of the liquid on the traveled surface.

In some embodiments the user can be presented with information, indications or output specifying or relating to the freezing point of liquid on the traveled surface rather than information, indications or output relating to the quantity of the one or more de/anti-icer moieties. In embodiments the user can be presented with information, indications or output specifying or relating to the freezing point of liquid on the traveled surface and than information, indications or output relating to the quantity of the one or more de/anti-icer moieties.

In some embodiments, the user can be provided with a definitive value for the amount of the de/anti-icer moiety/moieties remaining on the traveled surface, such as a specific concentration figure or a specific freezing point. In other embodiments, the user may not be provided with a definitive value for the amount of the de/anti-icer moiety/moieties remaining on the traveled surface, such as a specific concentration figure or a specific freezing point. In these other embodiments, the user can be provided with a representative value (such as a number from an arbitrary numerical scale) or an indication (such as a visual indication).

A representative value or visual indication may simply advise a user that the concentration or amount of the de/anti-icer moiety/moieties is, or is not, an appropriate concentration or amount, or that concentration or amount of the de/anti-icer moiety/moieties is, or is not, within an appropriate range. Similar considerations apply with respect to the indication of the freezing point of liquid on the traveled surface.

Whether or not the determined concentration or amount of the de/anti-icer moiety/moieties, or the determined freezing point, is appropriate, or is in an appropriate range, is typically assessed in the light of prevailing or expected weather conditions and/or the likely or intended use of the traveled surface.

The indication can be a visual indication in the form of a numeric or alphanumeric display, symbols, colour coding or the like. Where the visual indication is a colour the user can compare the colour with a colour reference chart to obtain final information about the concentration of the de/anti-icer moiety/moieties or about the freezing point of liquid on the traveled surface, as appropriate.

Alternatively, the indication can be in the form of a user-recognisable sound which can, for example, vary in pitch, pattern or rhythm in accordance with the determined concentration of the de/anti-icer moiety or moieties or in accordance with the determined freezing point of the liquid on the traveled surface.

The marker material can cooperate with a reader apparatus which provides the user-interpretable output. The output enables a user of the reader apparatus to discern and/or to assess the quantity (e.g. concentration or amount) of the de/anti-icer which remains on the traveled surface, or the freezing point of liquid on the traveled surface, in the light of prevailing or expected weather and in the context of the use of the traveled surface.

The marker material can react, interact with or cooperate with or cause a response in or with a reader device or apparatus. As noted, the reader apparatus can be configured or arranged to provide an output interpretable by a user. Thus the user can be informed and/or can judge whether or not the quantity of the de-icer or anti-icer composition on the traveled surface is appropriate for maintaining the traveled surface in a state which is wholly, substantially or sufficiently free from frozen water in the light of prevailing or expected weather conditions and in the context of the intended or likely use of the traveled surface.

The marker material can be selected so as to enable a user to determine or assess whether the quantity of the de-icer or anti-icer composition is appropriate for maintaining the traveled surface in a state which is wholly, substantially or sufficiently free from frozen water in the light of prevailing or expected weather conditions and in the context of the intended or likely use of the traveled surface.

Some embodiments of the present invention relate to de-icer compositions and/or anti-icer compositions which are formulated to include a de-icing or anti-icing substance or moiety (or a combination of such substances or moieties) and a marker material by means of which marker material a user is enabled to assess, judge or determine the quantity of the de-icing or anti-icing substance or moiety (or a combination of such substances or moieties) on a traveled surface at a selected time period after application of the de-icer or anti-icer composition to the surface.

In some embodiments a reader apparatus can be configured to cooperate with a marker material, said marker material being previously applied to a traveled surface in a composition comprising the marker material and a de-icing or anti-icing substance or moiety (or a combination of such substances or moieties), the reader apparatus being operative to provide an output interpretable by a user by which the user may determine the quantity of the de-icing or anti-icing substance or moiety on the traveled surface, or the freezing point of liquid on the traveled surface.

In further embodiments of the present invention can relate to de-icer compositions and/or anti-icer compositions which are formulated to include a de-icing or anti-icing substance or moiety (or a combination of such substances or moieties) and a marker material by means of which marker material a user is enabled to assess, judge or determine whether or not the de-icer or anti-icer composition is present in an effective amount on the traveled surface.

In further embodiments, the present invention can relate to a reader apparatus configured to cooperate with a marker material, said marker material being previously applied to a traveled surface in a composition comprising the marker material and a de-icing or anti-icing substance or moiety (or a combination of such substances or moieties), the reader apparatus being operative to provide an output interpretable by a user by which the user is informed and/or can judge whether or not the de-icer or anti-icer composition is present in an effective amount on the traveled surface.

In yet further aspects and embodiments, the present invention can relate to a reader apparatus configured for use in conjunction with a de/anti-icer composition which composition comprises a de-icing or anti-icing substance or moiety (or a combination of such substances or moieties) and a marker material. The apparatus can comprise: (a) detector means contactable with a liquid sample at, on, or obtained from, a traveled surface to which surface the de/anti-icer composition has been applied; and (b) a visual indication or display configured to provide a user-interpretable output based on a determined quantity from the detector means of the marker material in the liquid sample, by which output the user can be enabled to judge, assess or determine the quantity of said de/anti-icer composition on the traveled surface at a given time or by which output the user can be enabled to judge, assess or determine the freezing point of liquid on the traveled surface.

An "effective amount" is an amount of de-icer composition or anti-icer composition remaining on the traveled surface which is appropriate for maintaining the traveled surface in a state which is operationally safe for the passage thereover of pedestrians or vehicles (such as aircraft), as appropriate to the intended purpose of the traveled surface. An operationally safe state of the traveled surface is achieved when the traveled surface is sufficiently free from (e.g. wholly or substantially free from) frozen water in the light of prevailing or expected weather conditions and in the context of the intended or likely use of the traveled surface, such that the traveled surface may be used for its intended use without an unacceptable degree of risk attributable to the presence of frozen water.

Embodiments of the present invention can also comprise a system for treating a traveled surface, the system comprising a de-icer composition or an anti-icer composition including said marker material, and a reader apparatus.

Further embodiments of the present invention can include a method for treating a traveled surface, wherein the method can comprise applying a de-icer composition or an anti-icer composition including said marker material to the traveled surface.

Some embodiments of this method include using a reader apparatus configured to cooperate with said marker material to determine or measure the quantity of said marker material on the traveled surface, such measurement informing an operator or user of the corresponding quantity of the de-icer or anti-icer composition on the traveled surface and/or whether or not the de-icer or anti-icer composition is present in an effective amount on the traveled surface, or such measurement informing an operator or user of the freezing point of liquid on the traveled surface.

In yet another embodiment the present invention relates to a method of determining or measuring the quantity of a de-icer or anti-icer substance or moiety (or a combination of such substances or moieties) on a traveled surface, following application to said traveled surface of a composition comprising the de-icing or anti-icing substance or moiety (or a combination of such substances or moieties) and a marker material. The method can comprise using a reader apparatus configured to cooperate with said marker material to measure the quantity of said marker material on the traveled surface wherein the measurement can inform an operator or user of the corresponding quantity of the de-icer or anti-icer composition on the traveled surface and/or whether or not the de-icer or anti-icer composition is present in an effective amount on the traveled surface.

Further embodiments the present invention can be a method for preventing the formation of frozen water on a traveled surface and/or for removing frozen water from the traveled surface. The method can comprise applying to the surface a de/anti-icer composition comprising at least one de/anti-icer moiety and a marker material, and subsequently analysing a sample of liquid from the traveled surface to determine the quantity of marker material in the sample.

In embodiments the above method can further comprises determining that the amount of the marker material is below an effective amount and applying to the traveled surface further de/anti-icer composition.

Another embodiments the present invention can be a method of determining or measuring the freezing point of a liquid on a traveled surface, following application to said traveled surface of a composition comprising a de-icing or anti-icing substance or moiety (or a combination of such substances or moieties) and a marker material, the method comprising using a reader apparatus configured to cooperate with said marker material to measure the quantity of said marker material on the traveled surface, and informing the operator by an output of said reader apparatus based on said measurement of the freezing point of liquid on the traveled surface.

In yet further embodiments the present invention can be a system for analysing a sample of liquid from a traveled surface, wherein the system can comprise: (i) a de/anti-icer composition for application to the traveled surface comprising one or more de/anti-icer moieties and a marker material; and (ii) a test substrate, web or strip configured to receive, after application to the traveled surface of said de/anti-icer composition, said sample of liquid from the traveled surface, and including analysis apparatus configured to interact with said marker material for determining the concentration or amount of said marker material in said sample of liquid; (iii) a reader device configured to cooperate with test substrate to provide a user-comprehensible output based on a determination of the concentration of the marker material in the said sample of liquid said output being indicative of the concentration of said one or more de/anti-icer moieties in the said sample of liquid and/or of the freezing point of said sample of liquid.

Another embodiments the present invention can be a system for analysing a sample of liquid from a traveled surface, wherein the system can comprising (i) a de/anti-icer composition for application to the traveled surface comprising one or more de/anti-icer moieties and a marker material; and (ii) a test substrate, web or strip configured to receive said sample of liquid from the traveled surface after application to the traveled surface of said de/anti-icer composition, and including analysis means configured to interact with said marker material and to provide a visual indication (which can be a colour change) indicative of the concentration of said one or more de/anti-icer moieties in the said sample of liquid and/or of the freezing point of said sample of liquid. The analysis means can usefully comprise one or more chemicals applied to the substrate, web or strip and configured or selected to interact chemically with the marker material.

In yet further embodiments, the present invention can be a kit of parts comprising: (i) a de/anti-icer composition comprising one or de/anti-icer moieties and a marker material representative of the concentration of the one or more de/anti-icer moieties when the composition has been applied to a traveled surface; and (ii) one or more indicator substrates (such as test strips) responsive to the amount of marker material in a sample of liquid taken from the traveled surface to provide a user with a user-interpretable response indicative of said de/anti-icer moiety concentration and/or of the freezing point of said liquid.

In some embodiments said response can be a colour change.

In some embodiments, the kit of parts can further comprise a colour reference source against which the colour of said indicator strip is compared to determine said concentration or said freezing point. The colour reference source can be a printed paper, sheet, ticket, card or placard or the like, or can be in electronic form.

In the above aspects and embodiments of the invention, the marker material can be selected from the group comprising: glucose; alcohols; completely or partially water soluble salts of aluminium, ammonia or ammonium salts; ascorbic acid; completely or partially water soluble salts of calcium; carbonic acid salts; iodine; iodide salts; chlorine; chloride salts; bromine; bromide salts; fluorine; fluoride salts; completely or partially water soluble salts of cobalt; completely or partially water soluble salts of copper; formaldehyde; paraformaldehyde; reducing sugars other than glucose; starch; glutardialdehyde; ketones; aldehydes; completely or partially water soluble salts of iron; completely or partially water soluble salts of manganese; completely or partially water soluble salts of molybdenum; completely or partially water soluble salts of nickel; nitrate salts of one or more of potassium, sodium, lithium, magnesium, calcium, aluminium, iron and zinc; nitrite salts of one or more of potassium, sodium, lithium, magnesium, calcium, aluminium, iron and zinc; salts of peracetic acid; hydrogen peroxide; organic peroxides; phosphate salts of one or more of potassium, sodium, lithium, magnesium, calcium, aluminium, iron and zinc; quaternary ammonium compounds; sulphate salts of one or more of potassium, sodium, lithium, magnesium, calcium, aluminium, iron and zinc; sulphite salts of one or more of potassium, sodium, lithium, magnesium, calcium, aluminium, iron and zinc; completely or partially water soluble salts of zinc; proteins; and peptides or amino acids.

In some cases, chlorine or chloride salts may be deemed not meet the requirement that materials used in airside locations at airports do not have any substantial corrosive effect on materials commonly used in aircraft. Thus, in embodiments of the invention the marker material is other than chlorine or chloride salts. That is, in embodiments of the invention the marker material does not include, comprise, or consist of chlorine or chloride salts.

The de/anti-icer composition(s) of, or in, aspects or embodiments of the present invention can include one or more auxiliary or incidental additives. In some embodiments such auxiliary or incidental additives are selected from one or more of corrosion inhibitors, stabilisers, viscosity modifiers, surfactants, pH buffers, and anti-foaming agents. In some embodiments, the auxiliary or incidental additives can include one or more dyes.

As used herein, the term "auxiliary or incidental additive" is be a component of the composition, present in a relatively small amount (relative to the amount of the de/anti-icer moiety), the primary intended purpose (as recognized by a person skilled in the art) of which is other than the depression of freezing point. Thus an auxiliary or incidental additive can be included to modify properties (which may be initial properties or post-application properties) of the composition of the invention other than those connected directly with de-icing or anti-icing. Given the wide range of possible auxiliary or incidental additives, it is possible that a given auxiliary or incidental additive can have some freezing point depressing effect, however such effect can be generally de minimis compared with that of the de/anti-icer moiety or moieties, notably in view of the small amount of such additive which is present in the composition. Notable auxiliary or incidental additives include corrosion inhibitors.

In some embodiments said one or more incidental or auxiliary additives can be a corrosion inhibitor or a combination of corrosion inhibitors. In embodiments, the corrosion inhibitors can be those known to inhibit corrosion of aircraft parts with which the de/anti-icer composition can come into contact during use.

In some aspects and embodiments of the invention, the marker material can be water soluble. In some embodiments the marker materials can have a minimum water solubility of about 10 mgl$^{-1}$ at 20° C.

In some embodiments, the de/anti-icer composition of the invention can be colourless. In particular in these embodiments the marker material included in the de/anti-icer composition can be colourless.

In other embodiments the de/anti-icer composition of the invention can be blue in colour. In particular in these embodiments the marker material included in the de/anti-icer composition can be blue in colour.

In some embodiments, the de/anti-icer composition of the invention does not include any dye or other colour imparting material or compound. In particular in these embodiments the marker material included in the de/anti-icer composition does not include any dye or other colour imparting material or compound. By exception to the generality of the foregoing statement, in certain embodiments the de/anti-icer composition according to the invention may be coloured blue by a dye or other colour imparting material or compound.

In some embodiments the marker material can be selected from glucose, completely or partially water soluble salts of iron; completely or partially water soluble salts of zinc; carbonic acid salts, formaldehyde, starch, and phosphate salts of one or more of potassium, sodium, lithium, magnesium and calcium.

In some embodiments, the marker material can be glucose.

In some embodiments the marker material can be a carbonic acid salt.

In some embodiments the marker material can be a completely or partially water soluble salt of zinc.

In some embodiments the marker material can be a completely or partially water soluble salt of iron.

The marker material can be present in an amount of from about 0.001% w/w to about 0.2% w/w, such as in an amount from about 0.01% w/w to about 0.04% w/w.

In some embodiments the one or more de/anti-icer moieties can be selected from the group comprising ethylene glycol, propylene glycol, urea, alkali metal formate salts, alkali metal acetate salts or alkali metal acetate/formate salt mixtures.

In some embodiments the one or more de/anti-icer moieties can comprise one or more alkali metal formate salts.

In some embodiments the one or more de/anti-icer moieties can consist essentially of one or more alkali metal formate salts.

In some further embodiments the one or more de/anti-icer moieties can comprise one or more alkali metal acetate salts.

In some further embodiments the one or more de/anti-icer moieties can consist essentially of one or more alkali metal acetate salts.

In some embodiments the one or more de/anti-icer moieties can comprise alkali metal acetate/formate salt mixtures.

In some embodiments the one or more de/anti-icer moieties can consist essentially of alkali metal acetate/formate salt mixtures.

In these embodiments, the alkali metal can be potassium or sodium, and in particular potassium.

Thus in some embodiments the one or more de/anti-icer moieties can be potassium formate or potassium acetate, or a mixture of potassium formate and potassium acetate.

In some embodiments the one or more de/anti-icer moieties can be sodium formate or sodium acetate, or a mixture of sodium formate and sodium acetate.

In embodiments, the one or more de/anti-icer moieties can be selected from about 40 to about 60% w/w potassium acetate, about 40 to about 60% w/w potassium formate and about 40 to about 60% w/w potassium formate/acetate mixtures. In certain embodiments, the one or more de/anti-icer moieties can be selected from about 50% w/w potassium acetate, about 50% w/w potassium formate and about 50% w/w potassium formate/acetate mixtures. Here again, the corresponding sodium salts may be used as an alternative to the potassium salts.

In some embodiments the one or more de/anti-icer moieties can comprise:
at least about 25% w/w of at least one acetate salt selected from the group consisting of potassium, sodium, lithium, magnesium, calcium, ammonium acetate or mixtures thereof;
and
from about 14% to about 50% w/w of at least one non-acetate salt consisting of one or more cations selected from the group consisting of potassium, sodium, lithium, magnesium, calcium, ammonium or mixtures thereof and one or more anions selected from the group consisting of formate, propionate, butyrate, isobutyrate, oxalate, malonate, succinate, glutarate, adipate, citrate, gluconate, benzoate, carbonate, bicarbonate, fluoride, chloride, bromide or mixtures thereof;
the balance being solvent and optionally not more than about 5% w/w in total of one or more auxiliary or incidental additives,
wherein the total concentration of said at least one acetate salt and said at least one non-acetate salt in the de-icer or anti-icer composition is at least about 57% w/w.

In embodiments, the anion of the non-acetate salt is selected from the group consisting of formate, propionate, butyrate, isobutyrate, oxalate, malonate, glutarate, adipate, citrate, gluconate, benzoate, carbonate, bicarbonate, fluoride, chloride, bromide or mixtures thereof. In these embodiments, the anion of the non-acetate salt is other than succinate. Succinate may have the property of making the de/anti-icer composition somewhat slippery and therefore such composition can be unsuitable for use on traveled surfaces.

Embodiments of the invention can utilise a test strip which can be contacted with a sample of liquid from the traveled surface, or which can be contacted directly with liquid on the traveled surface. The test strip can comprise a web of material, typically fabricated as a paper, card or a plastic substrate, which carries chemical and/or electrical means for analysing the marker material contained in the liquid sampled from the traveled surface. In certain embodiments test strip can comprise a web of material fabricated as a plastic substrate.

in certain embodiments the web of material forming the test strip can be sufficiently rigid to prevent substantial deformation under its own weight.

In some embodiments, a typical test strip can have a length not more than about 10 cm and width not more than about 1.5 cm. In other embodiments, the test strip can have a length of not more than 8 cm. In another embodiment, the test strip can have a length of not more than 5 cm. In further embodiments, the test strip can have a width of not more than 1 cm. In yet further embodiments, the test strip can have a width of not more than 0.5 cm.

in some embodiments the test strips can be re-usable. With a view to simplicity of use and accuracy of the obtained reading, in some embodiments the test strips are can be disposable.

In some embodiments, when using a test strip, a sample volume of less than 5 ml can be sufficient for testing. In other embodiments, when using a test strip, a sample volume of less than 1 ml can be sufficient. In other embodiments, when using a test strip, a sample volume of less than 500 µl can be sufficient. In further embodiments, when using a test strip, volume of 50 µl or less can be sufficient.

In certain embodiments, quantitative analysis of the liquid from (or on) the traveled surface results in an output interpretable by the user. In some embodiments, the output can be derived from the amount of the marker material in the liquid and thereby can provide required information to the user relating to the presence, absence, concentration or amount of the de/anti-icer moiety.

In other embodiments, semi-quantitative analysis of the liquid from (or on) the traveled surface can result in an output interpretable by the user. In some embodiments, the output can be derived from the amount of the marker material in the said liquid and thereby can provide required information to the user relating to the presence, absence, concentration or amount of the de/anti-icer moiety.

In some embodiments the quantitative analysis can involve interaction or reaction of the marker material with one or more chemicals applied to the test strip. In some embodiments a series or cascade of reactions may be involved before a suitable output is attained. In other embodiments, the semi-quantitative analysis can involve interaction or reaction of the marker material with one or more chemicals applied to the test strip. In still other embodiments, a series or cascade of reactions can be involved before a suitable output can be attained.

In some embodiments, the test strip can carry one or more enzymes or enzyme derived materials which have specificity of reaction with the marker material. That is, in these forms it can be that the enzyme or enzyme derived material does not react with components of the sample other than the marker material.

In other embodiments, an acid-base neutralisation reaction can be employed. The acid or base can be applied to the test strip and the base or acid respectively can be the marker material. In these embodiments the output for the user can be derived from the pH following the acid-base neutralisation reaction which occurs on contacting the liquid from the traveled surface with the test strip. In some embodiments the pH can be determined electrochemically. In some embodiments the pH can be determined by use of a known pH indicator substance or composition.

Thus, in embodiments, depending on the choice of marker material and the corresponding choice of chemical(s) on the substrate, the output can be a colour change on the substrate or an electrical output to a suitable reader device.

As noted, the output from the test strip can provide the user with information relating to the amount or concentration of the de/anti-icer material in the liquid sample placed on the test strip, or relating to the freezing point of the liquid sample placed on the test strip, these being based on or derived from the determined concentration or amount of the marker material in the liquid sample.

In the case of an electrical output, the test strip can comprise an electrochemical micro-cell into which the liquid sample is placed, the concentration of the marker material thus being measured electrochemically.

In other embodiments, the marker material can be glucose and the test strip can be constructed to react with the glucose to provide an output to the user which can be based on, or derived from, the concentration or amount of glucose in the sample liquid.

Suitable chemical processes by which an amount or concentration of glucose in a sample can be processed to achieve a colour-based output representative of that amount are known in the art. In one example a glucose peroxidise can be used to convert glucose into gluconic acid and hydrogen peroxide. The hydrogen peroxide can oxidise a chromogen compound, for example, which can initially be colourless, into a dyestuff, in the presence of a peroxidatively active material (such as a peroxidise enzyme). The dyestuff can thus provide the desired colour change, the extent of the colour change can be, in turn, dependent on the position of an equilibrium between the chromogen and the dyestuff. Suitable chromogen compounds include, but are not limited to, 3,3',5,5'-tetraalkylbenzidines where alkyl represents C1 to C4. In some embodiments, alkyl can be methyl.

In the case of electrochemical methods, typically an electrochemical cell is provided with a working electrode and a reference electrode. The glucose bearing sample of liquid from the traveled surface can be placed in the cell where it undergoes a selective oxidation, typically catalysed by a suitable enzyme. A mediator molecule can transfer the electrons liberated by the selective oxidation to the working electrode. The amount of glucose can be calculated on the basis of the resulting electrical current (typically of the order of $\mu A$), or, in some variations on the charge. Enzymes used in this sort of process can include glucose oxidase, PQQ-glucose dehydrogenase, NAD-glucose dehydrogenase and FAD-glucose dehydrogenase. PQQ, NAD and FAD respectively refer to electron transferring co-factors. Suitable mediators can include, for example, ferricyanide and its derivatives and 1,10-phenanthroline quinone and its derivatives.

in some embodiments a test strip utilising an acid-base neutralisation reaction can employ a carbonate (i.e. a carbonic acid salt) as the marker material. The test strip can carry a suitable acid. Preferably the test strip can be porous or fibrous so that it contains cavities, interstices or voids into which the acid can be impregnated. In one example, the test strip can be made from a cellulosic material. The acid can be such as to readily crystallise in a solid form in said cavities, voids or interstices of the test strip. The acid must remain stable on the test strip during storage (provided that necessary storage conditions are met, such as limits with respect to ambient temperature and humidity, for example). One suitable acid is citric acid but other acids can be contemplated.

In some embodiments the test strip can also carry a suitable pH indicator substance. Numerous pH indicator substances are known and a suitable pH indicator can be selected on the basis of the anticipated pH range when the test strip is saturated with the liquid sample under test. For the carbonate-citric acid system, one suitable indicator can be Bromothymol Blue.

When the test strip carrying the acid and pH indicator is contacted with the liquid obtained from the traveled surface, the carbonate marker in said liquid can neutralise or partly neutralise the acid carried on the test strip, thereby changing the pH of the liquid and thus causing a colour change of the Bromothymol Blue indicator. The resulting colour can be indicative of the amount of carbonate marker in the liquid from the traveled surface and can be consequently indicative of the amount of de/anti-icer material in said liquid.

In the case of a colour based output, the user can be provided with a reference source including a range of coloured panels each panel being associated with a particular concentration of the marker material. The user can compare the colour obtained on the test strip against the reference source and can thereby determine the concentration or amount of the marker material and consequently the concentration or amount of the de/anti-icer moiety in the liquid sample from the traveled surface. In certain embodiments the reference source is can be calibrated in terms of the concentration or amount of the de/anti-icer moiety or the freezing point of the liquid sample, so that the user does not need to know directly any information relating to the amount or concentration of the marker material.

The reference source can be provided directly on the test strip or can be provided on packaging associated with the test strip, such as the container in which the test strips are provided. Alternatively, the reference source can be a separate printed paper, sheet, ticket, card or placard, or can be in electronic form.

In the case of an electrical output, a test strip can carry electronic circuitry which connects to an electrical reader device which in turn provides the user output.

As noted, knowing the concentration or amount of the de/anti-icer material can enable the user to know the freezing temperature of the liquid on the traveled surface, so that corrective action can be taken if necessary to prevent freezing on the traveled surface.

The output to the user can also, or alternatively, be presented as a freezing temperature (that is, a temperature at which the liquid on the traveled surface will freeze).

The following non-limiting examples are illustrative of de/anti-icer compositions according to the invention.

Example 1

50% w/w Potassium Acetate
0.5% w/w Ascorbic Acid
0.1% w/w n-Hexylamine
0.1% w/w Disodium Molybdate
0.02% w/w D-Glucose
Water to 100%
At pH 10.5-11.5

Example 2

50% w/w Potassium Formate
0.2% w/w Amino Tris (Methylene Phosphonic Acid)
0.3% w/w Triethanolamine
0.1% w/w Mercaptobenzothiazole
0.02% w/w D-Glucose
Water to 100%
At pH 10.5-11.5

Example 3

30% w/w Potassium Acetate
35% w/w Potassium Formate
0.5% w/w Dipotassium Suberate
0.23% w/w Monoisopropanolamine
0.04% w/w Disodium Hydrogen Phosphite
0.027% w/w D-Glucose
Water to 100%
At pH 10.5-11.5

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A ground surface de/anti-icer composition comprising:
   one or more de/anti-icer moieties; and
   a marker material, the marker material being selected such that, after application of the de/anti-icer composition to the ground surface, a concentration of the one or more de/anti-icer moieties on or proximate the ground surface at a given time can be determined from a quantity of the marker material on or proximate the ground surface at the given time;
   wherein the marker material is selected from the group consisting of glucose, completely or partially water-soluble salts of iron; completely or partially water-soluble salts of zinc; carbonic acid salts, formaldehyde, starch, and phosphate salts of one or more of potassium, sodium, lithium, magnesium and calcium; and
   wherein the ground surface de/anti-icer composition is configured such that application of the de/anti-icer composition on the ground surface does not decrease the surface friction of the ground surface over that of the ground surface without the application of the de/anti-icer composition by any more than an equal amount of liquid water would decrease the surface friction of the ground surface over that of the ground surface without the application of water.

2. The ground surface de/anti-icer composition as claimed in claim 1, wherein the ground surface de/anti-icer composition is colorless.

3. The ground surface de/anti-icer composition as claimed in claim 1, wherein the marker material is water soluble.

4. The ground surface de/anti-icer composition as claimed in claim 1, wherein the marker material is present in a quantity of from about 0.001% w/w to about 0.2% w/w.

5. The ground surface de/anti-icer composition as claimed in claim 1, wherein one or more de/anti-icer moieties is selected from the group consisting of ethylene glycol, propylene glycol, urea, alkali metal formate salts, alkali metal acetate salts and alkali metal acetate/formate salt mixtures.

6. The ground surface de/anti-icer composition as claimed in claim 1, wherein one or more of the de/anti-icer moieties comprises one or more alkali metal formate salts.

7. The ground surface de/anti-icer composition as claimed in claim 1, wherein one or more of the de/anti-icer moieties comprises one or more alkali metal acetate salts.

8. The ground surface de/anti-icer composition as claimed in claim 1, wherein one or more of the de/anti-icer moieties comprises alkali metal acetate/formate salt mixtures.

9. The ground surface de/anti-icer composition as claimed in claim 1, wherein one or more of the de/anti-icer moieties comprises one or both of potassium and sodium.

10. The ground surface de/anti-icer composition as claimed in claim 1, wherein one or more of the de/anti-icer moieties comprises:
    at least about 25% w/w of at least one acetate salt selected from the group consisting of potassium, sodium, lithium, magnesium, calcium, ammonium acetate and mixtures thereof; and from about 14% to about 50% w/w of at least one non-acetate salt comprising one or more cations selected from the group consisting of potassium, sodium, lithium, magnesium, calcium, ammonium or mixtures thereof and one or more anions selected from the group consisting of formate, propionate, butyrate, isobutyrate, oxalate, malonate, succinate, glutarate, adipate, citrate, gluconate, benzoate, carbonate, bicarbonate, fluoride, chloride, bromide and mixtures thereof; and wherein the balance comprises solvent.

11. The ground surface de/anti-icer composition as claimed in claim 1, wherein the marker material is present in a quantity of about 0.001% w/w to about 0.2% w/w; and
wherein one or more of the de/anti-icer moieties is selected from the group consisting of ethylene glycol, propylene glycol, urea, alkali metal formate salts, alkali metal acetate salts and alkali metal acetate/formate salt mixtures.

12. The ground surface de/anti-icer composition as claimed in claim 11, wherein one or more of the de/anti-icer moieties comprises:
at least about 25% w/w of acetate salt; and
from about 14% to about 50% w/w of non-acetate salt;
wherein the total concentration of acetate salt and non-acetate salt in the de/anti-icer composition is at least about 57% w/w.

13. The ground surface de/anti-icer composition as claimed in claim 11, wherein the marker material is glucose.

14. The ground surface de/anti-icer composition as claimed in claim 10 further comprising not more than about 5% w/w in total of one or more auxiliary or incidental additives; and
wherein the total concentration of acetate salt and non-acetate salt in the de/anti-icer composition is at least about 57% w/w.

* * * * *